United States Patent
Steuerwald et al.

(10) Patent No.: US 8,347,742 B2
(45) Date of Patent: Jan. 8, 2013

(54) SAMPLER

(75) Inventors: Ralf Steuerwald, Eberdingen (DE); Karl-Heinz Bareiss, Lorch (DE); Norbert Wandrei, Stuttgart (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 625 days.

(21) Appl. No.: 12/084,848

(22) PCT Filed: Nov. 16, 2006

(86) PCT No.: PCT/EP2006/068577
§ 371 (c)(1), (2), (4) Date: Aug. 5, 2009

(87) PCT Pub. No.: WO2007/057432
PCT Pub. Date: May 24, 2007

(65) Prior Publication Data
US 2009/0293645 A1 Dec. 3, 2009

(30) Foreign Application Priority Data

Nov. 17, 2005 (DE) .......................... 10 2005 055 284

(51) Int. Cl.
*G01N 1/00* (2006.01)
*G01N 1/14* (2006.01)
(52) U.S. Cl. ................ 73/863.11; 73/864.34; 73/864.35
(58) Field of Classification Search ............... 73/863.11, 73/864.34, 864.35, 864.73
See application file for complete search history.

(56) References Cited

U.S. PATENT DOCUMENTS

| 2,348,806 | A | | 5/1944 | Gillard |
|---|---|---|---|---|
| 3,250,130 | A | * | 5/1966 | Lozano ........................ 73/864.34 |
| 3,795,347 | A | * | 3/1974 | Singer ......................... 73/864.35 |
| 3,897,687 | A | | 8/1975 | Burberry |
| 4,628,748 | A | * | 12/1986 | Jogan et al. ................. 73/863.01 |
| 5,299,141 | A | | 3/1994 | Hungerford |
| 5,519,635 | A | | 5/1996 | Miyake |
| 5,537,336 | A | * | 7/1996 | Joyce ............................ 702/108 |
| 5,587,926 | A | | 12/1996 | Chiu |
| 6,880,413 | B2 | * | 4/2005 | Zeller ......................... 73/863.11 |
| 7,140,264 | B2 | * | 11/2006 | Zeller ......................... 73/863.11 |
| 7,152,664 | B2 | | 12/2006 | Kauschke et al. |
| 2005/0016299 | A1 | | 1/2005 | Zeller |
| 2005/0214165 | A1 | * | 9/2005 | Babel et al. ...................... 422/63 |
| 2006/0051238 | A1 | * | 3/2006 | Steuerwald et al. ............. 422/63 |

FOREIGN PATENT DOCUMENTS

| CN | 1653339 A | | 8/2005 |
|---|---|---|---|
| DE | 30 12 294 A1 | | 10/1981 |
| DE | 199 25 453 A1 | | 12/1999 |
| DE | 199 45 669 A1 | | 4/2001 |
| DE | 101 54 663 A1 | | 5/2003 |
| DE | 102 27 032 A1 | | 11/2003 |
| DE | 10 2004 015 083 | | 10/2005 |
| EP | 1 059 519 A | | 12/2000 |
| WO | WO 03/098198 | * | 11/2003 |

* cited by examiner

*Primary Examiner* — Daniel Larkin
(74) *Attorney, Agent, or Firm* — Bacon & Thomas, PLLC

(57) ABSTRACT

A sampler for automatic taking of liquid samples from a sample-taking location. The sampler includes: a housing with a door; an energy or power supply unit; a control/evaluation unit; a sample-taking unit, which, in a predeterminable time interval, takes a predetermined quantity of sample from the sample-taking location; a sample collecting unit arranged in a lower region of the housing of the sampler for storing taken samples; and a temperature-control unit, which controls at least the region of the sampler, in which the sample collecting unit is arranged, to a predetermined temperature.

16 Claims, 4 Drawing Sheets

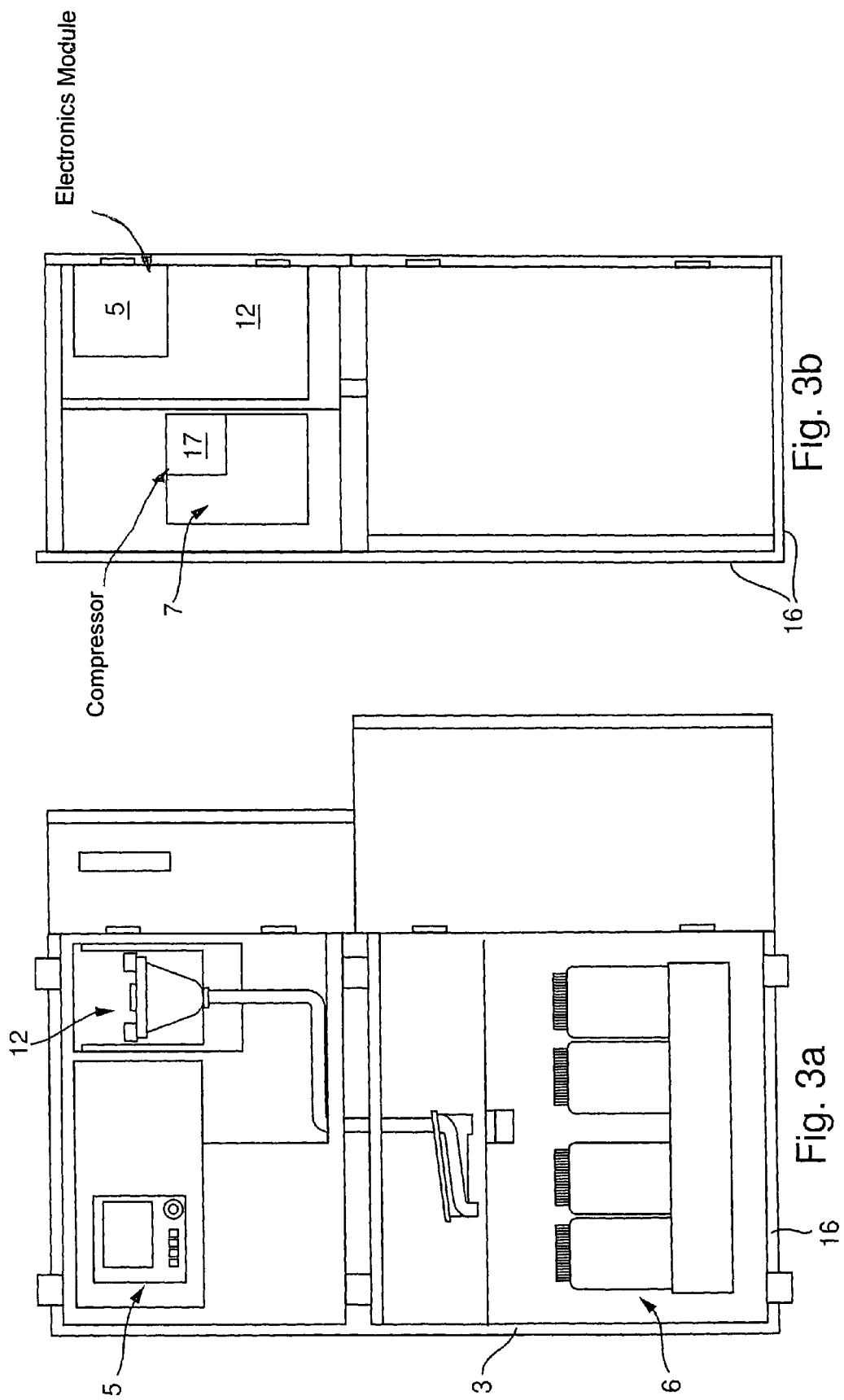

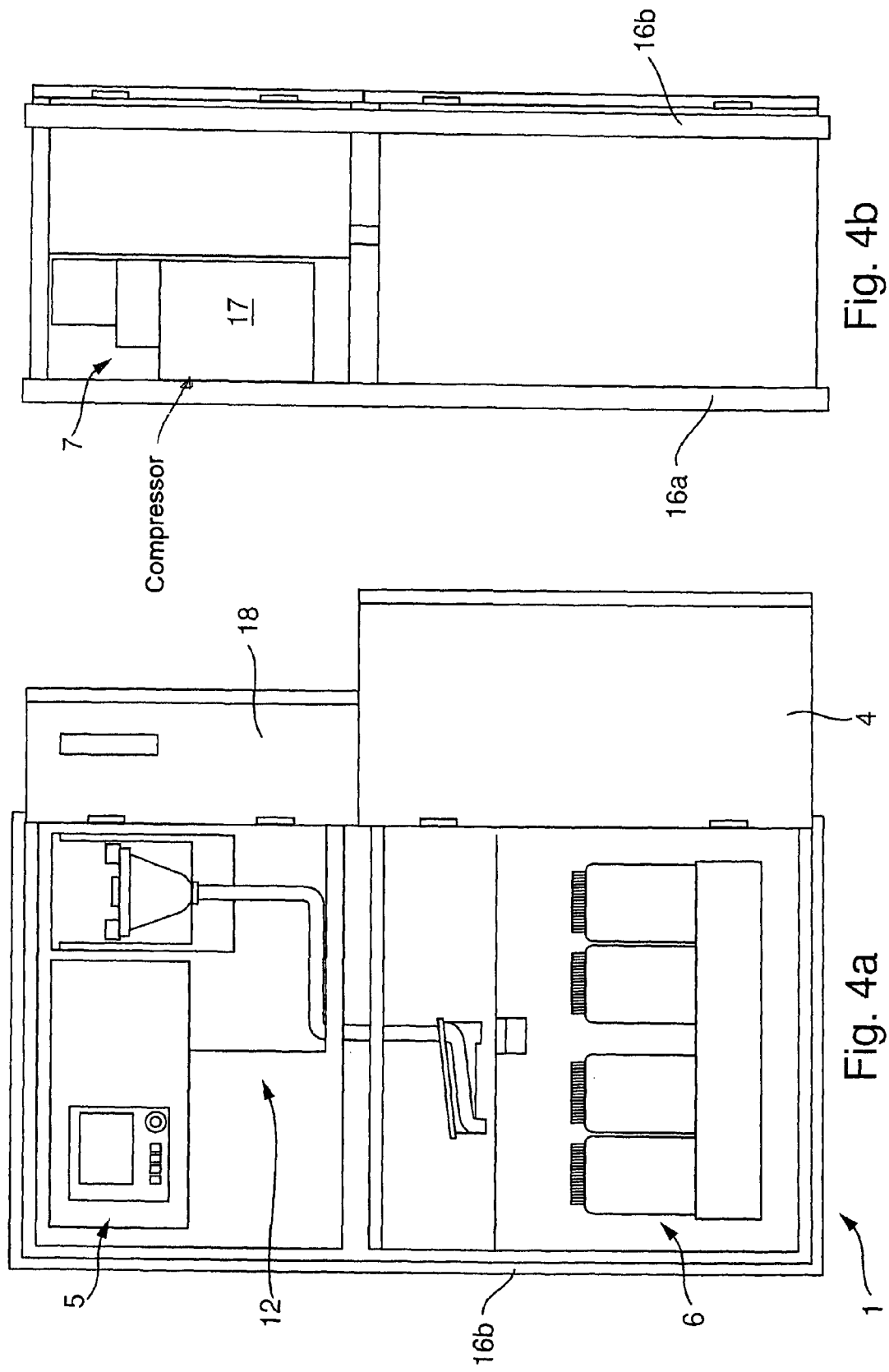

SAMPLER

TECHNICAL FIELD

The invention relates to a sampler for automatic taking of liquid samples from a sample-taking location.

BACKGROUND DISCUSSION

DE 102 27 032 A1 discloses a modularly constructed online-analyzer. Online analyzers are used for, among other applications, monitoring and optimizing the cleaning performance of clarification plants, monitoring activation basins and flow from a clarification plant, or in the control of filling material metering. Preferably, they monitor the amount of ammonium, phosphate or nitrate in a sample. Analysis of a sample is done, in such case, using known methods of measurement. Corresponding measuring devices for analysis of measurement samples are marketed and distributed by the present assignee.

An essential advantage of online analyzers is that they provide, over longer periods of time, at defined intervals, measured data as regards a monitored process variable. They are able e.g. to provide daily curves of data. Daily curves of data provide reliably, on the one hand, desired information as regards the ongoing operation of a plant; on the other hand, information as regards possibly required changes in the chemical engineering of the plant become available. On the basis of the analysis data, for instance, significant savings in operating equipment and costs accrue.

The online analyzer described in DE 102 27 032 A1 contains at least the following exchangeable modules:

A function module, which is embodied in such a manner that it provides measurement signals, which represent at least one physical or chemical, process variable; the function module is, for example, an ion-selective measuring apparatus or a colorimetric measuring apparatus. The colorimetric measuring apparatus is either a photometer or a spectrometer;

a pump module, which is embodied in such a manner that it supplies, into the function module in predetermined cycles, depending on the particularly applied function module, a predeterminable sample quantity and/or a predeterminable amount of at least one reagent or a predeterminable amount of a cleaning agent; and an electronics module, which controls the working cycles of the particularly applied pump module and/or the particularly applied function module, evaluates the measurement signals delivered by the function module, and provides the corresponding analysis data for the sample.

The known solution makes possible change or replacement of individual modules dedicated to the desired measurement parameters and measurement methods, in order to implement the most varied of analyzer types with a minimum number of different modules. Also known from the cited state of the art is to arrange a cooling module in the housing of the online analyzer for cooling reagents and/or the sample, as required.

Moreover, from U.S. Pat. No. 5,587,926, a cooled sampler is known, in the case of which the compressor of the cooling unit is arranged in the upper region of the housing of the sampler. Such an arrangement is to achieve that the cooled region of the housing, in which the samples are stored, is not influenced by the heated air cast off from the compressor. By integrating the cooling unit in the sampler, it becomes well suited for outside setups in the immediate vicinity of the sample-taking location. Disadvantageous in the known solution is that the operator has to decide already when ordering the sampler whether cooling is needed or not; a later changing or retrofitting is no longer possible or possible only with considerable technical and financial sacrifice. Disadvantageous also is that, in the case of a defective cooling unit, the complete housing must be replaced; at least, however, individual components of the cooling unit must be exchanged.

Also known is to install analyzers, for the purpose of cooling, in enclosures or measurement houses, which are air-conditioned. It has also been attempted to avoid this quite expensive solution by providing the analyzers in the form of immersible or submersible probes. Immersible or submersible probes have, however, the disadvantage that they are relatively difficult to maintain, due to dirtying by the medium and due to the handling in the immediate environment of the medium.

SUMMARY OF THE INVENTION

An object of the invention is to provide a modularly constructed sampler, which is so embodied that it is positionable under any conditions in the immediate vicinity of the medium to be measured or monitored.

The object is achieved by a sampler composed at least of a housing with a door and having components as follows: an energy or power supply unit; a control/evaluation unit; a sample-taking unit, which, in predeterminable intervals of time, takes a predetermined sample quantity from the sample-taking location; a sample collecting unit arranged in the lower region of the housing of the sampler for storing the taken samples; and a temperature-control unit, which controls at least the region of the sampler, in which the sample collecting unit is arranged, to a predetermined temperature, so that the sampler is applicable under any thermal conditions at the sample-taking location. The sampler of the invention is thus best suited for outside set-up and distinguishes itself moreover by the fact that it can be matched flexibly to given demands.

In a preferred embodiment of the apparatus of the invention, it is provided that the temperature-control unit is arranged in a separate housing module. Preferably, the housing module is thermally insulated. Especially, an adapter unit is provided, with which the separate housing module with temperature-control unit is adaptable to an outer surface of the sampler. Preferred variants for applying the housing module to the housing of the sampler include applying the temperature-control unit to one of the sidewalls of the housing of the sampler, under the sampler, or on top of the sampler. An embodiment of the temperature-controlled unit as a separate, connectable unit has the advantage that it enables optimum matching of the sampler to the conditions reigning at the site of the sample taking. If sufficient room is available as regards height, then it makes sense to arrange the housing module and the housing of the sampler one on top of the other. Preferably, the housing of the sampler and the housing module adjoining the sampler and accommodating the essential components of the temperature-control unit are thermally insulated from one another.

An option, thus, is to equip a sampler or also an online analyzer with a separate cooling or air-conditioning or temperature-control module, which can be easily installed and uninstalled on the housing of the sampler or online analyzer. The temperature-control module is highly integrated and contains the complete functionality of a temperature-control apparatus in a compact manner of construction. Especially, an option is to equip the sampler or online-analyzer subsequently with the temperature-control module. In the case of instances of service, the module can very easily be exchanged. In general, it can be said that the modularly constructed sampler, or the cooled online analyzer, can be matched very flexibly to the special wishes of a customer. Customer-specific solutions can be implemented rapidly, cost-effectively and simply.

An advantageous embodiment of the sampler of the invention provides at least one securement plate, to which the housing of the sampler and/or the housing module with the temperature-control unit can be secured. The securement plate is, or the securement plates are, arranged on the rear side and/or on at least a side wall of the housing of the sampler and/or the housing module with the temperature-controlled unit. Especially, the housing module with the temperature-control unit is secured above the housing of the sampler to the securement plate or plates.

In an advantageous embodiment of the apparatus of the invention, it is provided that an analysis apparatus is placed in the housing for analyzing, online, the taken samples. In this way, an on-site analysis is possible at the measurement location, in direct connection with the supplying of the samples. Due to the shorter paths, the measurement results are correspondingly more quickly available; additionally, times of accessing the process are shorter. Also, the high capital costs for measuring huts, measuring containers and the like are avoided.

By the modularity of the components, the apparatus of the invention can be matched individually to customer-specific needs. Thus, it can happen, that, at a present point in time at a defined measurement location, only one sample-taking is to be performed. At a later point in time, it becomes necessary to analyze a process variable of taken samples on-site. Such changes of direction are possible without problem because of the modular construction. The sample-taking module can be removed and replaced or supplemented by a pump module and an analysis module.

To enable a simple matching of requirements specified by the customer, or user, it is additionally provided that the energy supply unit and/or the control/evaluation unit are/is embodied as an electronics module, which makes available all contemplated functionalities of the modularly constructed, online analyzer.

Moreover, it is provided that the sample-taking unit, including at least a suction tube, a pump and a distributor station for the samples, is modularly constructed. For example, the pump module can be a vacuum pump or a peristaltic pump.

In an advantageous embodiment of the apparatus of the invention, it is provided that the cooling/temperature-control module and the sample-taking unit form one unit, which is mechanically and/or electrically separated from the other parts of the sampler or analyzer.

BRIEF DESCRIPTION OF THE DRAWINGS

The invention will now be explained in greater detail on the basis of the appended drawing, the figures of which show as follows:

FIG. 3*a* is a front view of a schematic representation of a third embodiment having a securement plate in the rear region of the temperature-controlled sampler;

FIG. 3*b* is a side view of the third embodiment;

FIG. 4*a* is a front view of a schematic representation of a fourth embodiment having securement plates in the side region of the temperature-controlled sampler; and FIG. 4*b* is a side view of the fourth embodiment.

DETAILED DISCUSSION

Figure 1:
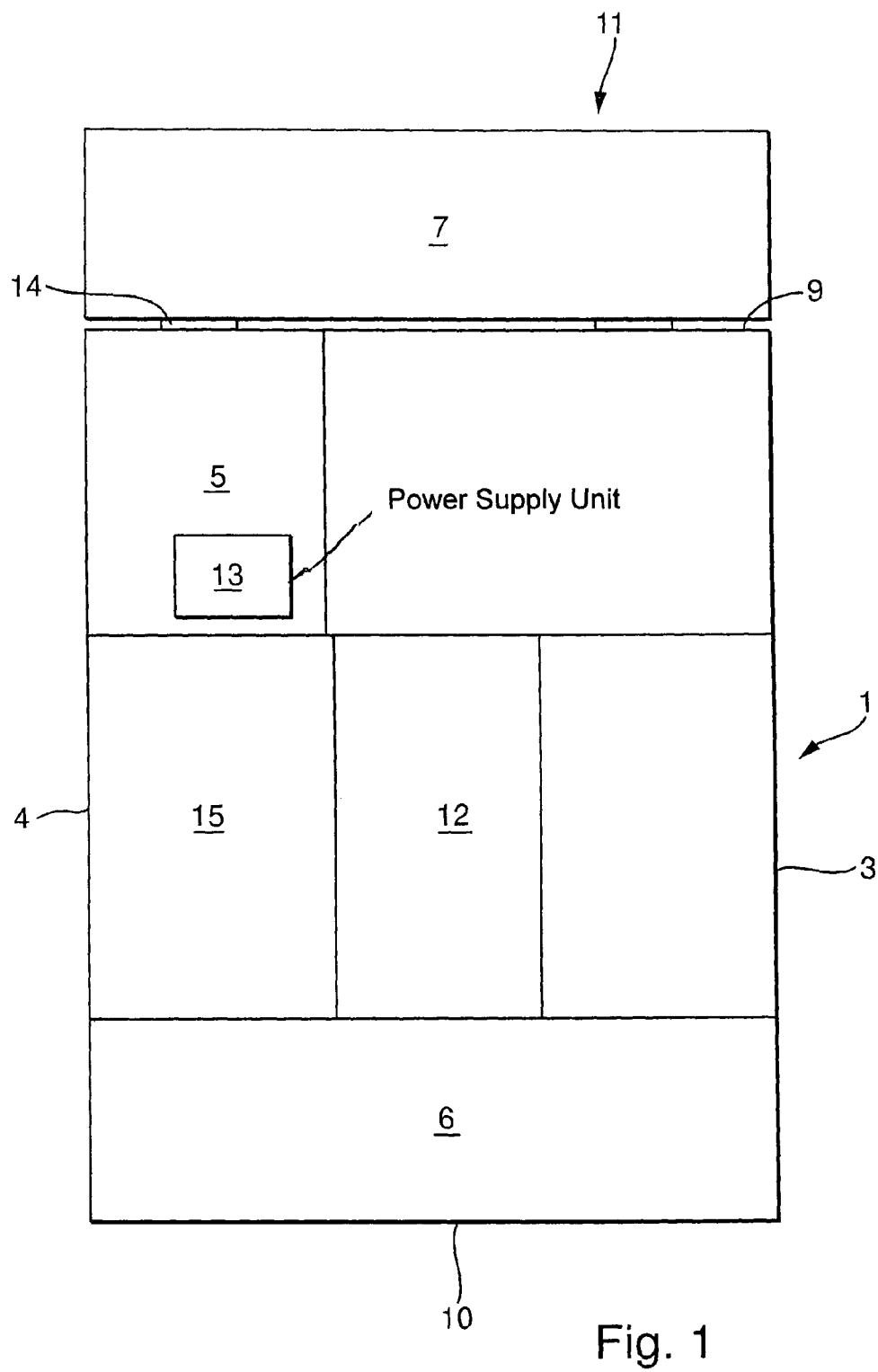
FIG. 1 is a schematic representation of a first embodiment of the sampler of the invention.

FIG. 1 shows a schematic representation of a first embodiment of the sampler 1 of the invention. Sampler 1 is constructed modularly and includes a housing 3 with a door 4 preferably located in the front region. In the housing 3 are the electronics module 5, composed of the energy or power supply unit 13 and a control/evaluation unit, separated from the so-called wet part. In this way, the sensitive electronics components are effectively protected from contact with the liquid sample. Preferably, the electronics module 5 is located in the upper region of the housing 3, while the wet space is located in the lower region of the housing 3. In the wet space are positioned the sample-taking unit 12, the sample collecting unit 6 with at least one collecting container, and the analysis module 15. The analysis module is matched to the particular process variable to be monitored. The sample-taking unit is composed of a suction tube, a pump, usually a peristaltic pump or a vacuum pump, and a sample distributor, via which the taken samples are filled into the at least one collecting container. The individual components are not shown in detail in FIGS. 1 and 2. However, these components are best known from a stationary sampler distributed by the firm, Endress+Hauser, under the name ASP-Station.

Spaced from the housing 3 of the sampler 1 is the housing module 11 with the temperature-control unit 7. In the case of the embodiment represented in FIG. 1, housing module 11 is mounted on the roof surface 9 of the housing 3 of the sampler 1. In the case of the embodiment shown in FIG. 2, housing module 11 is secured to the side wall 8 of the housing 3. Preferably, the securement of the housing module 11 is by way of a releasable connection. To this end, provided is an adapter unit 14, which, in the simplest case, is made of mutually engaging, insertion rails.

Figure 2:
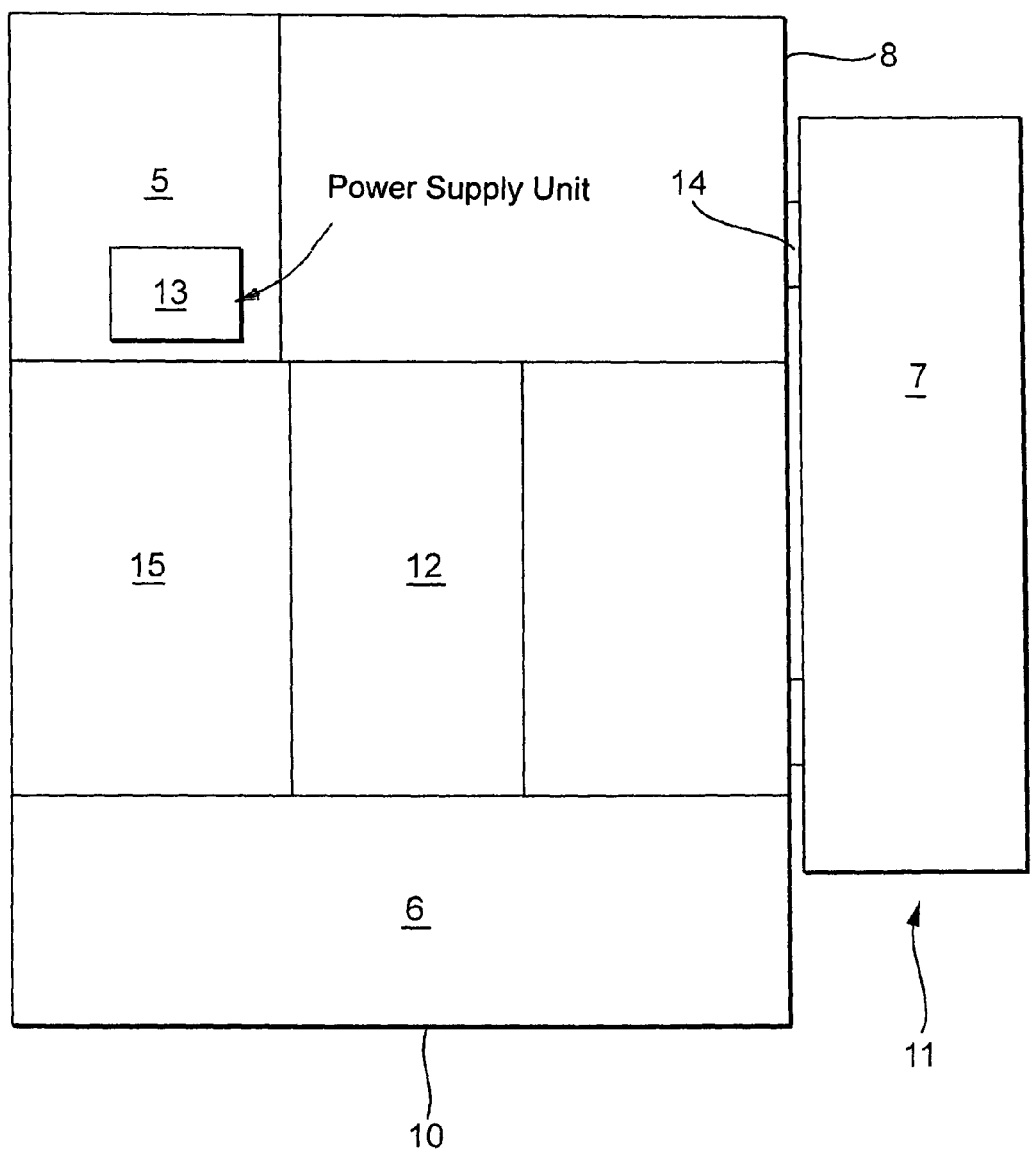
FIG. 2 is a schematic representation of a second form of embodiment of the sampler of the invention.

Electrical connection of the adjoining housing module 11 to the housing 3 of the sampler 1 is accomplished through an opening not specially shown in FIGS. 1 and 2. Preferably, the opening is so embodied that the electronics module 5 is protected by partitioning from the wet space.

FIG. 3*a* shows a schematic representation, in front view, with opened doors, of a third embodiment having a securement plate 16 in the rear and lower regions of the temperature-controlled sampler 1. FIG. 3*b* shows such in side view. Secured to the securement plate 16 are the housing 3 of the sampler 1 and, on top of such, the modularly embodied, temperature-control unit 7 with compressor 17, condenser and evaporator. At corresponding locations in the underside of the temperature-control unit 7 and the upper side of the housing 3 of the sampler 1, in each case, an opening is provided, via which a preferably insulated connection of the mechanical and/or, as required, the electrical connecting lines are provided between the two housings 3, 7. By embodying the temperature-control unit 7 as a module, it is possible to equip a sampler, even subsequently, with a temperature-control unit 7.

In the case of the front view shown in FIG. 4*a* of a fourth embodiment, two securement plates 16*a*, 16*b* are provided in the two side regions of the housing 3 of the sampler 1 and the temperature-control unit 7. FIG. 4*b* shows the embodiment in side view. Again, the two housing parts 3, 7 are separated from one another, with the temperature-control unit 7 being secured above the housing 3 of the sampler. The securement of the housing modules 3, 7 on the laterally provided securement plates 16a, 16b is done, preferably, via releasable, screwed connections, thus in a manner like that shown in FIG. 3. By the advantageous embodying of the temperature-controlled sampler 1 with modularly embodied, temperature-control unit 7, a temperature-controlled, or cooling, module 7 can be added or removed, according to need. The temperature-control module 7 is insulated thermally from the sampler 1 arranged in the housing 3.

The invention claimed is:

1. A sampler for automatic taking of liquid samples from a sample-taking location, comprising:
    at least one housing with at least one door;
    an energy, or power, supply unit; and
    a control/evaluation unit; said energy, or power, supply unit and said control/evaluation unit being arranged in said at least one housing;
    a sample-taking unit, which, in a predeterminable time interval, takes a predetermined quantity of sample from said sample-taking location;
    a sample collecting unit arranged in a lower region of said at least one housing for storing taken samples;
    a temperature-control unit, which is arranged in a separate housing module, said temperature-control unit controlling at least the region of the housing, in which said sample collecting unit is arranged, to a predetermined temperature; and
    an adapter unit, with which said separate housing module with said temperature-control unit is adaptable to an outer surface of the housing, wherein:
    said separate housing module and said at least one housing are thermally insulated from one another.

2. The sampler as claimed in claim 1, wherein:
    said at least one housing has a side wall, a roof surface, and a floor surface;
    said housing module with said temperature-control unit is arranged in mounted condition on said side wall of said at least one housing said at least one housing or on said roof surface of said at least one housing.

3. The sampler as claimed in claim 1, wherein:
    said at least one housing and said separate housing module of said temperature-control unit are thermally insulated.

4. The sampler as claimed in claim 1, wherein:
    at least one securement plate is provided, to which said at least one housing and said separate housing module with said temperature-control unit are connected.

5. The sampler as claimed in claim 4, wherein:
    said at least one securement plate, is provided on the rear side and/or on at least one side wall of said at least one housing.

6. The sampler as claimed in claim 5, wherein:
    said separate housing module with said temperature-control unit is secured above said at least one housing to the securement plate, or securement plates.

7. The sampler as claimed in claim 6, said temperature control unit comprising a compressor, condenser and evaporator.

8. The sampler as claimed in claim 1, further comprising:
    an analysis apparatus, wherein:
    said analysis apparatus is placed in said at least one housing and serves for performing an online analysis on a taken sample.

9. The sampler as claimed in claim 1, wherein:
    the energy or power supply unit and said control/evaluation unit are embodied as an electronics module, which is separated from a wet part of the sampler in the lower region of the housing, said wet part comprising the sample taking unit and the sample collecting unit.

10. The sampler as claimed in claim 1, wherein:
    said sample collecting unit comprising at least one collecting container, and
    said sample-taking unit comprising at least a suction tube, a pump and a distributor station via which the taken samples are filled into the at least one collecting container.

11. The sampler as claimed in claim 1, wherein:
    the energy or power supply unit and the control/evaluation unit are located in an upper region of the housing and separated from a wet part in the lower region of the housing, the wet part comprising the sample taking unit and the sample collecting unit.

12. The sampler as claimed in claim 1, said temperature control unit comprising a compressor, condenser and evaporator.

13. A sampler for automatic taking of liquid samples from a sample-taking location, comprising:
    at least one housing with at least one door;
    an energy, or power, supply unit;
    a control/evaluation unit;
    said energy, or power, supply unit and said control/evaluation unit being arranged in said at least one housing;
    a sample-taking unit, which, in a predeterminable time interval takes a predetermined quantity of sample from said sample-taking location;
    a sample collecting unit arranged in a lower region of said at least one housing for storing taken samples;
    a temperature control unit comprising a compressor, condenser and evaporator,
    said temperature control unit being arranged in a separate housing module, said temperature control unit controlling at least the region of the housing, in which said sample collecting unit is arranged to a predetermined temperature;
    wherein said separate housing module and said at least one housing are thermally insulated from one another, and
    wherein at least one securement plate is provided, to which said at least one housing and said separate housing module with said temperature control unit are connected,
    said separate housing module being arranged above said at least one housing to the securement plate.

14. The sampler as claimed in claim 13, said at least one securement plate is provided on the rear side and/or on at least one side wall of said at least one housing.

15. The sampler as claimed in claim 13, wherein:
    the energy or power supply unit and said control/evaluation unit are embodied as an electronics module, which is separated from a wet part of the sampler in the lower region of the housing, said wet part comprising the sample taking unit and the sample collecting unit.

16. The sampler as claimed in claim 15, wherein:
    said sample collecting unit comprising at least one collecting container, and said sample-taking unit comprising at least a suction tube, a pump and a distributor station via which the taken samples are filled into the at least one collecting container.

* * * * *